United States Patent [19]

Fleming, III

[11] Patent Number: 5,718,678
[45] Date of Patent: Feb. 17, 1998

[54] MULTI-LUMEN COAXIAL CATHETER AND METHOD FOR MAKING SAME

[75] Inventor: James Anthony Fleming, III, North Wales, Pa.

[73] Assignee: Medical Components, Inc., Harleysville, Pa.

[21] Appl. No.: 679,353

[22] Filed: Jun. 26, 1996

[51] Int. Cl.[6] .................................................. A61M 3/00
[52] U.S. Cl. .................................... 604/43; 604/280
[58] Field of Search ............................... 604/27, 29, 43, 604/48, 53, 93, 264, 280, 283, 4–6; 138/114, 112, 116, 137

[56] References Cited

U.S. PATENT DOCUMENTS

| | | |
|---|---|---|
| 3,394,705 | 7/1968 | Abramson . |
| 4,037,599 | 7/1977 | Raulerson . |
| 4,072,146 | 2/1978 | Howes . |
| 4,406,656 | 9/1983 | Hattler et al. . |
| 4,493,696 | 1/1985 | Uldall . |
| 5,053,004 | 10/1991 | Markel et al. . |
| 5,167,622 | 12/1992 | Muto . |
| 5,167,623 | 12/1992 | Cianci et al. . |
| 5,190,058 | 3/1993 | Jones et al. . |
| 5,207,648 | 5/1993 | Gross . |
| 5,221,255 | 6/1993 | Mahurkar et al. . |
| 5,221,256 | 6/1993 | Mahurkar . |
| 5,308,323 | 5/1994 | Sogawa et al. . |
| 5,378,230 | 1/1995 | Mahurkar . |

*Primary Examiner*—Corrine M. McDermott
*Assistant Examiner*—Deborah Blyveis
*Attorney, Agent, or Firm*—Panitch Schwarze Jacobs & Nadel, P.C.

[57] ABSTRACT

A multi-lumen coaxial catheter and method for making such a catheter are provided. The catheter includes three generally coaxially disposed catheter tubes having proximal and distal portions and defining three coaxial lumens. The distal portions are attached to the proximal portion of a sleeve. The distal portion of the sleeve extends outwardly from the proximal portion of the sleeve around the inner catheter tube to form a tip. The proximal portions of the catheter tubes are attached to a hub having passageways in fluid communication with the lumens extending longitudinally within the catheter tubes. The passageways are further in fluid communication with extension tubes also attached to the hub.

13 Claims, 6 Drawing Sheets

MULTI-LUMEN COAXIAL CATHETER AND METHOD FOR MAKING SAME

FIELD OF THE INVENTION

The present invention relates to a multi-lumen, coaxial catheter for use in transferring fluids to and from a catheterized area, including the ability to introduce medicaments to the area, and to a method of making such a catheter.

BACKGROUND OF THE INVENTION

Catheters may be located in various venous locations and cavities throughout the body. Central venous catheters, for example, are placed in four common locations within the chest and/or in the femoral vessels. They may be placed, for example, in either the right or left subclavian vein or in the right or left internal jugular vein.

Using landmarks, vessels are identified and may be cannulated by first aspirating the vessel with a long hollow needle to ensure the vessel has been properly located. When blood enters a syringe attached to the needle, the syringe is disconnected and a thin guide wire is passed through the needle into the hollow passage, or lumen, of the vessel. The needle is then removed leaving the guide wire within the vessel. The guide wire projects beyond the surface of the skin.

At this point, the simplest method of catheter placement is to pass a catheter into the vessel directly over the guide wire. The guide wire is then removed leaving the catheter in position within the vessel. If a large diameter catheter is used, a dilator device is first passed over the guide wire to enlarge the hole following which the catheter is passed over the guide wire and the guide wire and dilator removed.

Multi-lumen catheters for infusion, perfusion, hemodialysis and the like are known. Dual-lumen catheters used for hemodialysis, for example, provide one lumen for arterial (intake) flow of blood to be purified and one lumen for venous (return) flow of purified blood. Cross-sectional configurations of such dual-lumen catheters typically include: two semi-circular (or double-D) lumens arranged in a side-by-side configuration and formed within a unitary tube which is internally divided by a planar septum; two circular lumens arranged in a side-by-side configuration and formed within a unitary tube separated by a septum; circular and crescent-shaped lumens (or circle-C) arranged in a side-by-side configuration and formed within a unitary tube which is divided internally by a curved septum by attaching the exterior surface of an inner tube along its length to the interior surface of an outer tube; elliptically-shaped and circular lumens arranged in a side-by-side configuration and formed within a unitary tube divided by a curved septum; and circular and annular lumens arranged in a coaxial configuration wherein an inner tube is placed within an outer tube and the lumens are divided by the exterior surface of the inner tube.

Use of coaxial lumens enables the catheter to have multiple openings arranged circumferentially around the exterior of the catheter to access the outer, typically arterial, lumen. Generally, the fluid flowing in the opposite, typically venous, direction enters or leaves through one or more openings at the distal tip of the catheter. Due to the coaxial configuration, fluid flow entering and leaving the catheter is evenly distributed and/or centrally disposed with respect to the longitudinal axis of the catheter. This provides for a more stable catheter.

In hemodialysis applications, the evenly distributed flow characteristics minimize the tendency present in side-by-side lumens to pull to one side due to an unequal pressure created by the dialysis device when pulling blood inward. Unequal flow tends to pull the catheter to one side causing suction of the distal end of the catheter against the vessel wall. By equalizing and thereby centering flow, a coaxial catheter design contributes to minimizing potential harm to the vessel and the possibility of stenosis. The equal flow distribution also helps to center the catheter in the vessel and reduce overall vibration of the inserted distal portion of the catheter, typically resulting from unequal flow. By reducing vibration and centering the catheter in the vessel, the coaxial design reduces the chances of recirculation and suctioning to the vessel wall which may cause vessel trauma and/or blockage of the luminal openings. The circular cross-sections of the lumens also provide excellent fluid flow properties within the lumens due to the lack of corners which may slow the flow of blood at that portion of the lumen wall. Examples of coaxial, dual-lumen catheters may be found in U.S. Pat. Nos. 4,493,696, 4,037,599 and 5,053,004.

Triple lumen catheters which are used for infusion and hemodialysis, for example, are also known and include various cross-sectional configurations such as three independent non-coaxial circular tubes placed within a larger tube as in U.S. Pat. No. 4,072,146; a unitary tube having a planar septum dividing the interior of the catheter into two semicircular lumens, one of which is again divided in half by a second septum into two side-by-side circular arc-shaped lumens as in U.S. Pat. No. 5,221,255; a unitary tube with a septum forming two large, roughly elliptically shaped lumens and a small infusion lumen extending along the interior wall of the unitary tube as in U.S. Pat. Nos. 5,221,256; a unitary tube divided by a first septum into a large circular lumen and a crescent shaped lumen which is further divided by a second septum into two separate lumens; and a first dual-lumen catheter having a circular and crescent shaped-lumen attached along the length of its exterior surface to the interior surface of a larger tube thereby forming a third crescent-shaped lumen between the dual-lumen catheter and the larger tube as in U.S. Pat. No. 5,167,623.

While there have been attempts to form multi-lumen coaxial catheters having three or more lumens which can be used for hemodialysis and/or infusion of medicaments or other related catheter functions as in U.S. Pat. No. 5,207,648, such catheters have not achieved a configuration which includes a tip which sufficiently facilitates insertion using standard guide wire insertion techniques for chronic and acute catheterizations and which adequately takes advantage of the flow advantages of the coaxial configuration as described above.

Accordingly, there is a need in the art for such a multi-lumen coaxial catheter having openings which provide all the advantages of coaxial flow for performing functions such as hemodialysis, but which also successfully allows for the introduction of fluids, including medicaments, in conjunction with, or as an alternative to, those functions. There is also a need in the art for such a catheter having a tip which has sufficient structural integrity to facilitate insertion for chronic and acute catheterizations, but which is not vulnerable to being dislodged from the remainder of the catheter body. There is further a need for such a catheter that can function well for both acute and chronic catheterization procedures and for a method of making such a catheter.

SUMMARY OF THE INVENTION

The present invention includes a multi-lumen coaxial catheter. The catheter includes at least three coaxially disposed catheter tubes having proximal portions and distal portions and defining at least three lumens extending longitudinally within the catheter. The catheter also includes a sleeve and a hub. The sleeve has a proximal portion configured for attaching the distal portions of the catheter tubes together and a distal portion configured for forming a tip around the distal portion of at least one of the catheter tubes. The hub has at least three passageways each of which is in fluid communication with one of the lumens. At least three extension tubes are attached to the hub. Each of the extension tubes is in fluid communication with one of the at least three passageways. There is also at least one opening in each of the distal portions of the catheter tubes. Each of the openings is in fluid communication with at least one of the lumens.

In one embodiment, the invention includes a multi-lumen coaxial catheter which includes a first, second and third catheter tube, each tube having a proximal portion and a distal portion. The first catheter tube defines a first lumen extending longitudinally within the catheter from a proximal end to a distal end of the first tube. The second catheter tube is disposed generally coaxially around the first catheter tube, and the first and second catheter tubes define an annular second lumen extending longitudinally within the catheter from a proximal end to a distal end of the second tube. The third catheter tube is disposed generally coaxially around the second catheter tube, and the second and third catheter tubes define an annular third lumen extending longitudinally within the catheter from a proximal end to a distal end of the third tube. The catheter also includes a sleeve which has a distal portion and a proximal portion. The proximal portion of the sleeve is attached to the distal portions of the first, second and third catheter tubes to hold the first and second catheter tubes within the third catheter tube and to seal the second and third lumens at their distal portions. The third lumen is sealed proximally to the second lumen. The distal portion of the sleeve extends outwardly from the proximal portion of the sleeve and forms a tip around the distal portion of the first catheter tube. A first opening extends transversely through the third catheter tube, the sleeve and the second catheter tube and is in fluid communication with the second lumen. A second opening, proximal to the first opening, extends transversely through the third catheter tube and is in fluid communication with the third lumen. A third opening extends through the distal portion of the sleeve and is in fluid communication with the first lumen. A hub is provided which has a plurality of passageways each being in fluid communication with one of the first, second and third lumens. The catheter also includes a plurality of extension tubes each of which is in fluid communication with one of the passageways in the hub.

The invention also includes a method of making a multi-lumen coaxial catheter. The method includes providing a first catheter tube having a distal portion, a proximal portion and a first lumen extending therethrough, providing a second catheter tube having a distal portion and a proximal portion and placing the first catheter tube within the second catheter tube such that the first catheter tube and the second catheter tube are generally coaxially disposed and spaced from each other to define an annular second lumen. A sleeve is then attached to the distal portions of the first and second catheter tubes to seal the second lumen. A third catheter tube having a distal portion and a proximal portion is provided. The second catheter tube is placed within the third catheter tube such that the second catheter tube and the third catheter tube are generally coaxially disposed and spaced from each other to define an annular third lumen. A distal portion of the sleeve extends outwardly from the third catheter tube. The third catheter tube is attached to the sleeve to seal the third lumen. A first opening is formed in fluid communication with the second lumen. A second opening is formed which is proximally spaced from the first opening and in fluid communication with the third lumen. The outwardly extending distal portion of the sleeve is formed into a tip. A third opening is formed in the tip distal to the first and second openings and in fluid communication with the first lumen. First, second and third extension tubes are also provided. A hub is attached on the proximal portions of the first, second and third catheter tubes. The hub has a plurality of internal passageways each of which is in fluid communication with one of the first, second and third catheter lumens and one of the first, second and third extension tubes.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings, like numerals are used to indicate like elements throughout. In the drawings.

DETAILED DESCRIPTION OF PREFERRED EMBODIMENTS

Certain terminology is used in the following description for convenience only and is not limiting. The words "right," "left," "lower" and "upper" designate directions in the drawings to which reference is made. The words "proximal" and "distal" refer to directions away from and closer to, respectively, for example, the insertion end of the catheter in a preferred multi-lumen coaxial catheter according to the present invention. The terminology includes the words above specifically mentioned, derivatives thereof, and words of similar import.

Referring now to the drawings in detail, where like numerals indicate like elements throughout, there are shown in FIGS. 1 through 5B and 7, a preferred embodiment of a multi-lumen catheter, generally indicated as 10 having three lumens which are generally coaxial in configuration in use. As best shown in FIGS. 2–5B, the catheter 10 includes a first inner catheter tube 12 having a proximal portion 14 and a distal portion 16 which respectively terminate in a proximal end 18 and a distal end 20. The inner catheter tube 12 defines a longitudinally extending first lumen 22 which has a generally circular cross section and extends between the distal and proximal ends 18, 20 of the first tube 12. As shown in FIG. 5A, it is preferred that the distal end 20 of the first tube terminates at the distal terminus 24 of the catheter 10. Preferably, in the preferred embodiment shown in FIGS. 1 and 5B and 7, the first lumen is a return flow or infusion flow lumen for introduction of fluids and/or medications. However, it should generally be understood that the first lumen could be an intake lumen.

Figure 1:
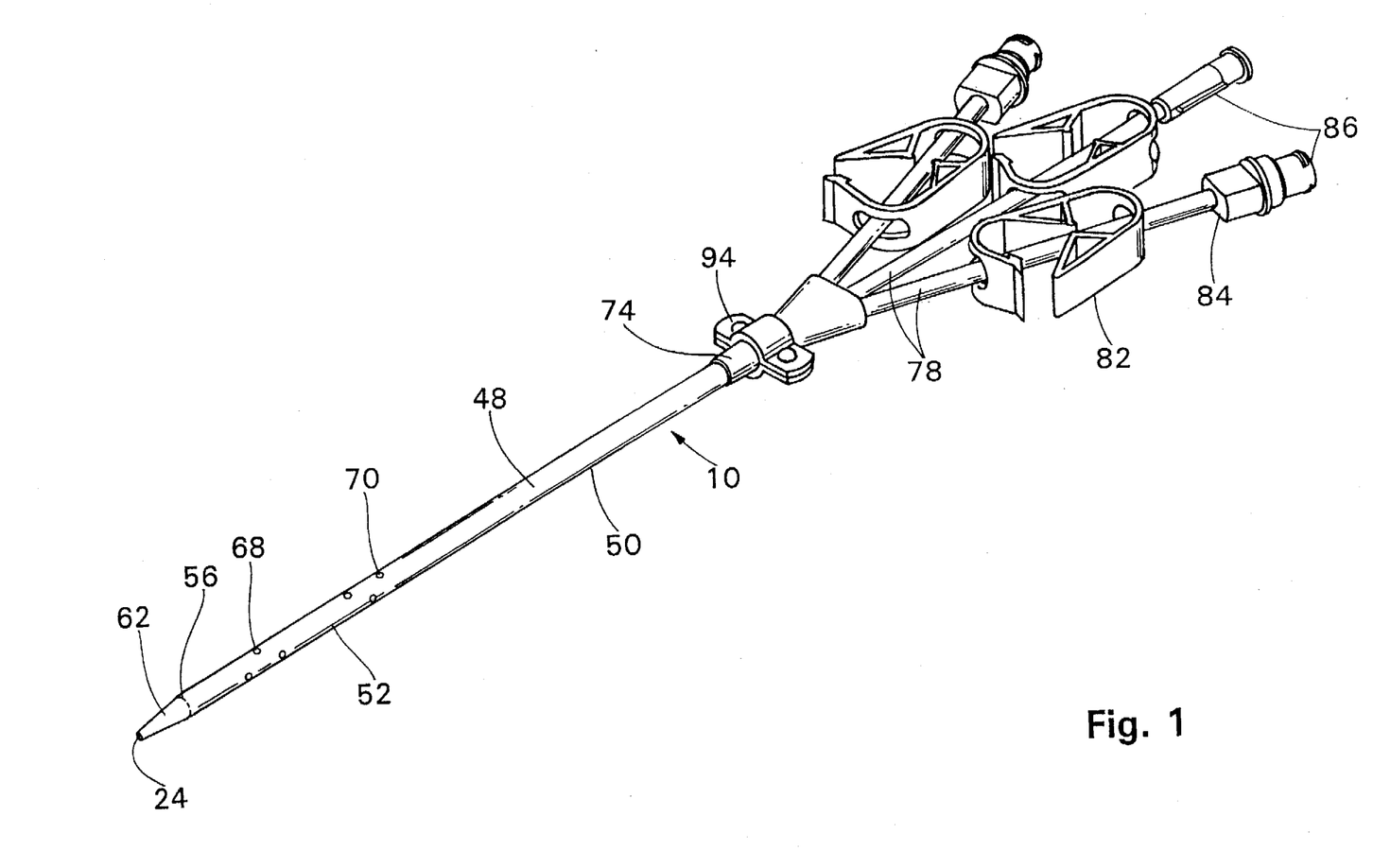
FIG. 1 is a perspective view of a preferred embodiment of a triple-lumen catheter according to the present invention.

A second intermediate catheter tube 26 is disposed generally coaxially around the first catheter tube 12 such that the interior surface 28 of the second tube 26 is spaced from the exterior surface 30 of the first tube 12 along the length of the second catheter tube. The second catheter tube 26 has a proximal portion 32 and a distal portion 34 which respectively each terminate in a proximal end 36 and a distal end 38. Preferably both the proximal and distal ends 18, 20 of the first catheter tube 12 extend beyond the proximal and distal ends 36, 38 of the second catheter tube 26. The second catheter tube 26 and the first catheter tube 12 together define a longitudinally extending second lumen 40 which extends from the proximal end 36 to the distal end 38 of the second tube 26. The second lumen 40 has a generally annular cross section. In the preferred embodiment as shown in FIGS. 1 and 5, when used for hemodialysis, the second lumen is preferably a return flow or venous flow. However, it should be understood that the second lumen can have a reverse flow direction, particularly if the catheter is used for other uses.

Figure 5A:
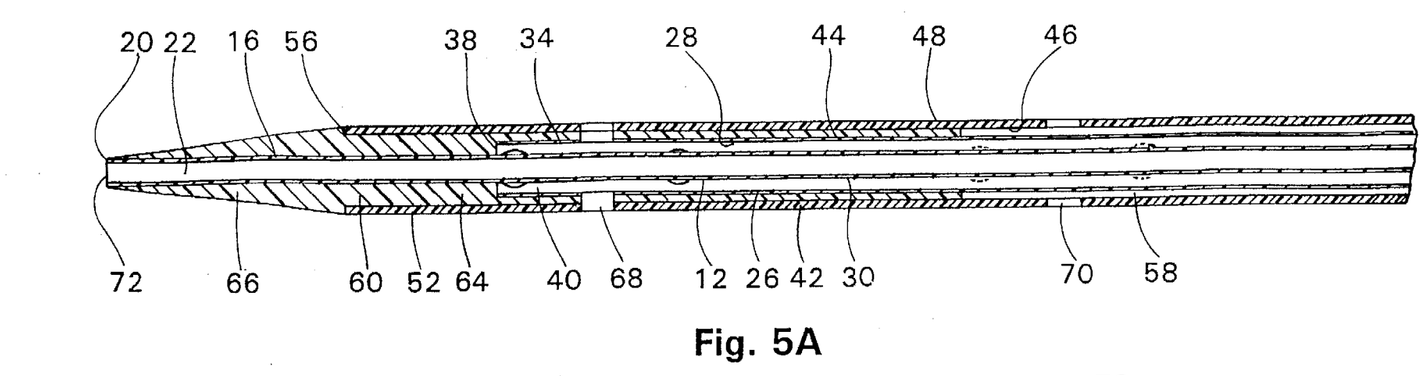
FIG. 5A is a partial sectional view of the catheter of FIG. 7 taken along line 5A—5A.

A third outer catheter tube 42 is disposed generally coaxially around the second intermediate catheter tube 26 such that the exterior surface 44 of the second catheter tube 26 is spaced from the interior surface 46 of the third catheter tube 42 along its length. In forming the triple lumen embodiment as shown in the drawings, the exterior surface 48 of the third tube 32 is the exterior surface of the catheter 10 as shown in Figs. 1 and 5A.

The third catheter tube 42 has a proximal portion 50 and a distal portion 52 which terminate respectively in a proximal end 54 and a distal end 56. Preferably, the distal end 56 of the third tube 32 extends beyond the distal end 38 of the second tube 26 but terminates proximally to the distal end 20 of the first catheter tube 12 as shown in FIG. 5A. It is further preferred that the proximal end 54 of the third tube is distal to the proximal ends 18, 36 of the first and second tubes. The second catheter tube 26 and the third catheter tube 32 together define a longitudinally extending third lumen 58 which extends from the proximal end 54 to the distal end 56 of the third tube 42. The third lumen 58 has a generally annular cross section and is used as an intake or arterial flow lumen in the preferred embodiment as shown in FIGS. 1 and 5. It should be understood, however, that the third lumen can function in the reverse flow direction as a venous lumen depending upon the particular use of the catheter.

The catheter tubes 12, 26, 42 may be formed of any suitable biocompatible polymer or elastomer, more preferably from a biocompatible polymer. Suitable biocompatible polymers include materials such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art. It should be understood that these possible biocompatible polymers are included above for exemplary purposes and should not be construed as limiting. If a biocompatible polymeric material is used to form the catheter tubes 12, 26, 42, it is more preferred that the polymeric material include a polyurethane or a polyolefin material.

Suitable, biocompatible elastomers which may be used in forming the catheter tubes 12, 26, 42 include biocompatible elastomers such as medical grade silicone rubbers, polyvinyl chloride elastomers, polyolefin homopolymeric and copolymeric elastomers, urethane-based elastomers, and natural rubber or other synthetic rubbers.

When forming a catheter for use in a small area, such as a blood vessel, the overall catheter diameter must be sized such that it fits comfortably within the vessel. This limits the maximum outer diameter of the catheter and, consequently, the diameter of each inner catheter tube. Further, in order to provide sufficient lumen area for flow of fluid, such as blood, through the lumens, it is desirable to form the thinnest walls possible while still maintaining adequate structural integrity and rendering the catheter resistant to kinking. Therefore, if the catheter is to be used in blood vessels and/or other smaller catheterization areas having specific flow requirements, it is preferred that the catheter tubes be formed of a first polyurethane which is resistant to kinking, has adequate structural integrity, is somewhat flexible and can be extruded to form desirably thin-walled tubes to provide maximum lumen area. An example of such a polyurethane includes Tecothane® which has a Shore durometer hardness of 55D.

It will be understood, based on this disclosure, that the catheter tubes 12, 26, 42 may also be provided with radiopacity by any suitable method such as by providing barium sulfate to the material used to form the tubes. Preferably about 20 wt % barium sulfate is provided to polyurethane prior to extruding the catheter tubes, particularly if the catheter is to be used for hemodialysis. Further reinforcing materials may also be provided. The length of the tubes 12, 26, 42 can be varied in accordance with the intended applications and general catheter sizes. The wall thickness of the inner tubes 12, 26 and the inner diameter of the inner tubes 12, 26 can also be varied depending on the intended use.

In determining the appropriate dimensions for hemodialysis applications, for example, the size of the area to be catheterized, in this case, a blood vessel, is a significant design factor which limits the size of the device. The vessel size determines the maximum outside diameter of the outside tube of the catheter. The catheter should not be the same size as the vessel as the access holes arterial holes 70 would become blocked by the vessel walls.

The catheter should be sized to leave a sufficient amount of space between the outside surface of the outer tube of the catheter and the inside surface of the vessel. Wall thicknesses and inner diameters of each of the tubes 12, 26, 42 must be selected so that the first, inner tube 12 fits within the second, intermediate tube 26 which, in turn, fits within the third, outer tube 42. The third tube 42 should have a diameter equal to, or less than, the maximum acceptable size. The tubes are, therefore, sized to provide sufficient lumen area within a predetermined maximum outer diameter size.

The preferred insertion site for the catheter 10, if used in a hemodialysis application, is the internal jugular vein. The maximum accepted diameter for a catheter in this particular vessel is 13 French or 0.170 in. It should be understood based on this disclosure, that the maximum accepted diameter will vary in accordance with the area, or specific vessel to be catheterized. To conduct hemodialysis, the wall thickness of the third tube 42 should be at least 0.015 to resist kinking of the catheter. This thickness could be decreased by provided reinforcing material. The first tube 12 and second tube 26 should be sized so that the second lumen 40 allow for flow of a volume of fluid which is the substantially the same as the volume of fluid flowing in the third lumen 58 at a given pressure. To accomplish this, the third lumen 58 should be approximately 10% larger than the second lumen 40. The first lumen 22 extending through the first tube 12 should be large enough to pass a 0.038 in guideware through the entire length of the lumen 22.

Based on the above criteria, in a preferred hemodialysis catheter for internal jugular use, the wall thickness of the inner tubes 12, 26 is preferably from about 0.076 mm to about 0.117 mm, and the inner diameters of the first and second tubes are respectively from about 0.965 mm to about 1.066 mm and from about 2.362 mm to about 2,463 mm. The third, or outer tube 42 is preferably somewhat thicker than the inner tubes. For use in hemodialysis applications for the internal jugular, the outer wall thickness of the third, outer tube 42 is preferably only from about 0.330 mm to about 0.431 mm and the inner diameter is preferably from about 3.378 mm to about 3.479 mm.

The catheter 10 also includes a sleeve 60 attached to the distal portions 16, 34, 52 of the first, second and third tubes and which is used to form a tip 62 on the distal portion 16 of the first catheter tube 12. The sleeve may be formed from any suitable polymeric material or elastomer such as those suitable for forming the catheter tubes. However, the sleeve 60 is preferably formed of a softer durometer material than the material used to form the tubes 12, 26, 42. Most preferably, the sleeve is formed of a second polyurethane of a softer durometer than the first polyurethane material used to form the catheter tubes. An example of such a polyurethane is a Tecothane® having a Shore durometer hardness of 85A. The sleeve is attached by heat molding, or more preferably, by insert molding. However, other methods of attachment such as, co-extrusion, ultrasonic welding or adhesive are also possible, although not preferred.

Figure 6A:
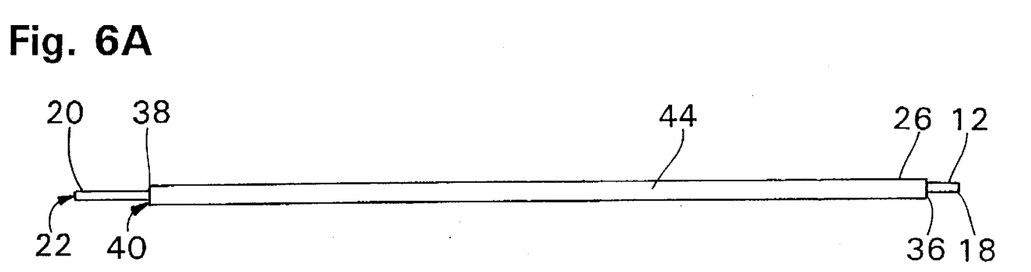
FIGS. 6A–6G represent the method steps of a preferred method of making a catheter according to the present invention.
Figure 6B:
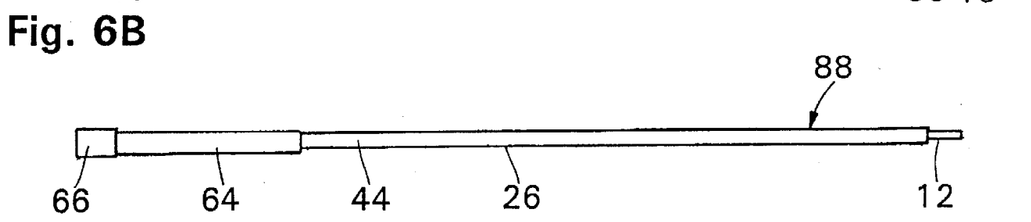

As shown in FIG. 6B, the sleeve 60 has an integral proximal portion 64 and distal portion 66. The distal portion 66 may be formed into the tip 62 by heat molding, grinding or other similar procedure. The tip 62 may have a variety of configurations including a blunt (or transversely flat) tip, a bullet-shaped tip, or a conical, tapered tip. For use in hemodialysis (particularly in acute hemodialysis procedures), it is preferred that a conical tip be provided to facilitate insertion of the catheter into the patient. The distal portion 66 preferably extends outwardly from the proximal portion 64 of the sleeve to the distal end 20 of the first catheter tube 12. As shown in the preferred embodiment in FIG. 5A, the distal portion 66 of the sleeve also extends outwardly from the distal end 56 of the third tube.

Figure 5B:
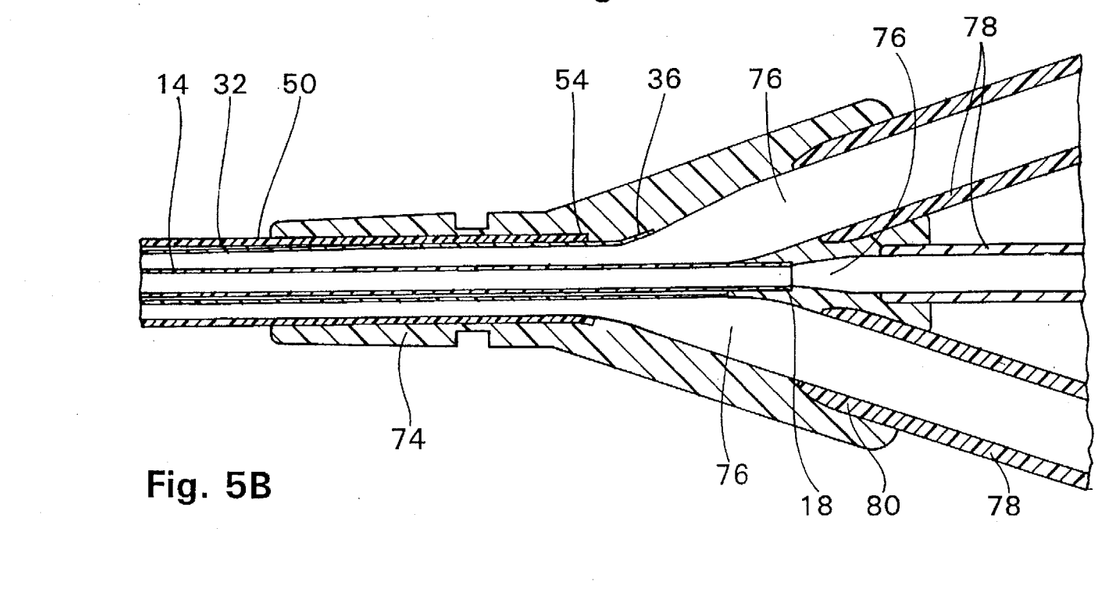
FIG. 5B is a partial sectional view of the catheter of FIG. 7 taken along line 5B—5B.

As shown in FIG. 5B, the proximal portion 64 of the sleeve 60 is configured to be attached to the distal portions 16, 34, 52 of the tubes. The proximal portion 64 is preferably molded or otherwise attached around the distal portions 16, 34 of the first and second tubes such that it seals off the second lumen 40 at the distal end 38 of the second tube. When the third tube 42 is placed around the first and second tubes, it is attached to the outside of the sleeve such that the third lumen 58 is sealed at the distal end 56 of the third tube and the first and second tubes 12, 26 are held within the third tube 42. Preferably, the third tube 42 is also molded to the sleeve 60. The sleeve also seals a portion of the third lumen 58 in the distal portion 52 of the third tube. The sleeve effectively seals the third lumen proximally to the second lumen. The purpose of sealing the lumens in this manner is for providing access holes to the lumens as shown in FIG. 5A.

At least one access opening is provided to the each of the lumens 22, 40, 58 at the distal portions of the tubes 12, 26, 42. A first opening 68, preferably a first plurality of openings 68 as shown in FIGS. 1 and 5A, extends transversely through the third catheter tube 42, the sleeve 60 and the second catheter tube 26. The opening 68 is preferably located such that it extends through the distal portion of the second tube 26 at the distal end 38 of the second tube and the distal end 38 forms a tangent to the opening 68. When more than one opening 68 is provided, the openings 68 are preferably spaced from each other in a helical configuration around the circumference of the third tube 42 with at least one of the openings 68 contacting the distal end 38 of the second tube such that the distal end 38 is tangent to the opening 68. The openings 68 extend through the third tube 42, sleeve 60 and second tube 26 such that they are in fluid communication with the second lumen 40.

A second opening 70, preferably a second plurality of openings 70 as shown in FIGS. 1 and 5, extends transversely through the third catheter tube 42. The opening 70 is preferably located such that it extends through the distal portion of the third tube 42 proximal to the sealed area of the third lumen 58 and the distal end 56 of the third tube 42 is tangent to the opening 70. When more than one opening 70 is provided, the openings 70 are preferably spaced from each other in a helical configuration around the circumference of the third tube 42 in the same manner as the openings 68, but proximal to the openings 68, and such that the distal end 56 of the third tube 42 is tangent to at least one of the openings 70. The openings 70 extend through the third tube 42 such that they are in fluid communication with the third lumen 58.

A third opening 72, or a plurality of openings (not shown) in the manner of openings 68, 70, extends through the distal portion 66 of the sleeve 60, or tip 62 and is in communication with the first lumen 22. The third opening may extend transversely through the tip 62 and tube 12 to the first lumen 22, or, as shown in FIG. 5A, may be formed longitudinally through the distal portion 66 of the sleeve at the distal terminus 24 of the catheter 10 in fluid communication with and coaxial with the first lumen 22. Preferably, if the tip 62 is tapered as shown in FIGS. 1 and 5A, the opening extends longitudinally through the tip 62 such that the tip 62 is frustoconically shaped.

The sleeve 60 is preferably sized to facilitate the desired longitudinal spacing between openings 68, 70, 72 in accordance with a particular application of use for the catheter. For example, for hemodialysis, it is preferred that the venous and arterial openings be sufficiently longitudinally spaced to prevent recirculation. Medicament delivery preferably also occurs downstream from any intake flow to prevent accidental removal of the medicaments entering the patient. In the preferred embodiment shown, the intake, or arterial, openings are designated 70 and are spaced from about 19.05 mm to about 20.32 mm from the return, or venous, openings designated 68. The preferred infusion opening 72 is preferably spaced from about 17.78 mm to about 20.32 mm from the openings 68.

The proximal portions 14, 32, 50 of the catheter tubes 12, 26, 42 are attached to a hub 74. The hub may be formed of any of the polymeric materials suitable for forming the sleeve 60 and preferably is formed of a heat moldable material of a similar durometer to that of the sleeve 60. Preferably, the hub is formed of a heat moldable polyurethane such as Pellethane® having a Shore durometer hardness of 80A. However, it will be understood by those of ordinary skill in the art, from this disclosure, that the hub 74 may be formed of any suitable polymeric material capable of being heat molded.

The hub 74 is preferably insert molded around the tubes such that the proximal ends 18, 36, 54 of the tubes are within the hub 74 and the lumens are in independent fluid communication with independent passageways 76 in the hub 74. A plurality of extension tubes 78 are attached to the proximal end of the hub 74 such that each extension tube 78 is in fluid communication with a passageway 76 in the hub and one of the lumens. As shown in FIG. 5B, the distal ends 80 of the extension tubes 78 are preferably molded within the hub.

Figure 2:
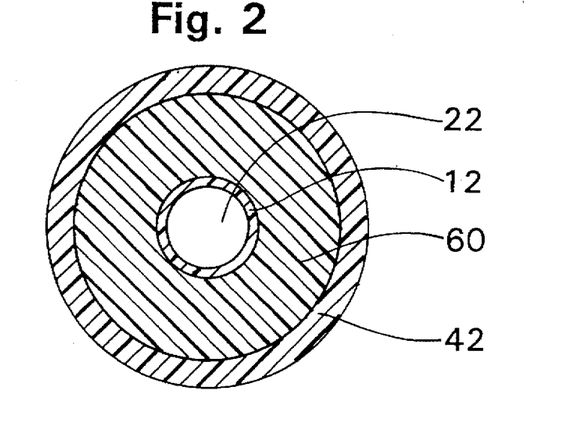
FIG. 2 is a cross-sectional view of the catheter of FIG. 7 taken along line 2—2.
Figure 3:
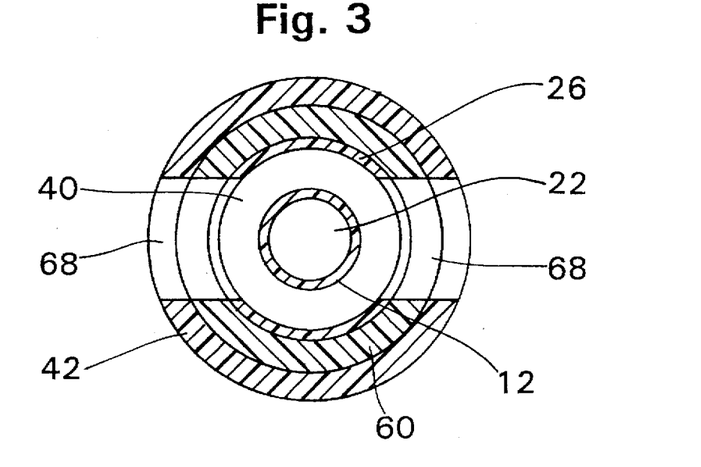
FIG. 3 is a cross-sectional view of the catheter of FIG. 7 taken along line 3—3.
Figure 4:
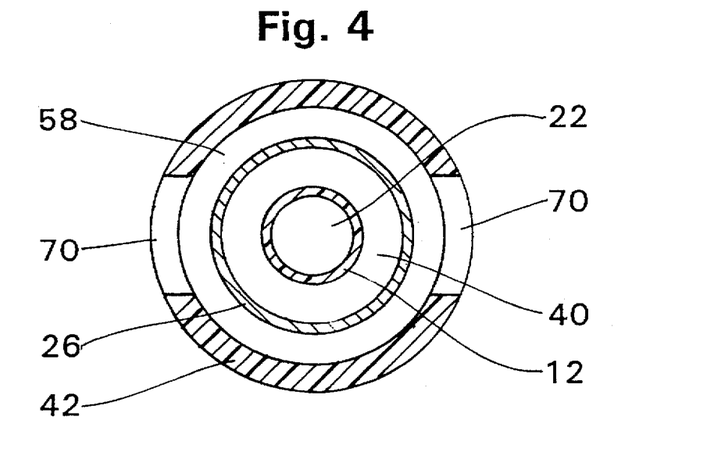
FIG. 4 is a cross-sectional view of the catheter of FIG. 7 taken along line 4—4.

While the catheter tubes are fixed in a substantially coaxial configuration as shown in FIGS. 2 and 3, over the majority of the length of the catheter tubes, the tubes are independent and movable with respect to each other. During use, however, pressure exerted by fluids flowing within the lumens contributes to holding the lumens in their predetermined coaxial configuration over the independent, otherwise movable portions of the tubes. At the proximal ends, in order to divert the independent fluids flowing within the coaxial lumens toward the independent extension tubes and passageways at the proximal end of the catheter, the proximal ends 36, 54 of the second and third catheter tubes 26, 42 are preferably slightly deflected within the hub 74 as shown in FIG. 5B. The first tube 12 continues coaxially through the hub 74. While there is a slight deflection in the second and third tubes as the lumens open into the passageways within the hub, the lumen configuration is generally coaxial along the length of the catheter tubes such that it should be understood that the term "coaxial" in this application includes a generally coaxial cross section and a configuration in which the catheters are substantially coaxial along their length.

Figure 7:
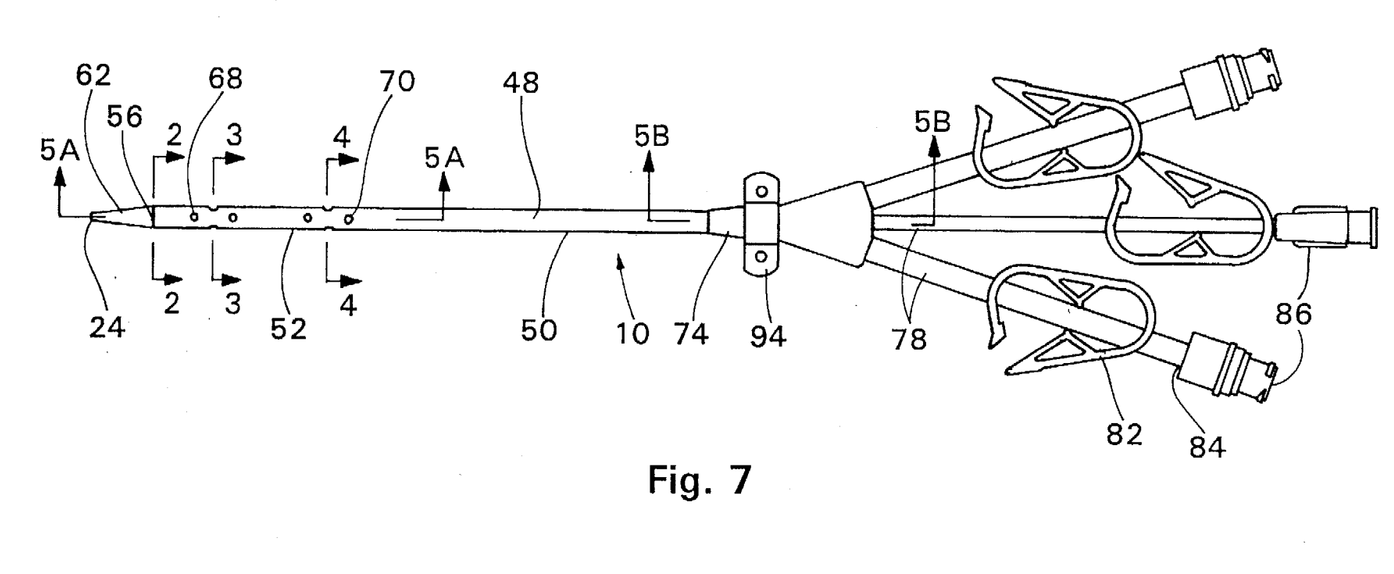
FIG. 7 is a plan view of a preferred embodiment of a triple-lumen catheter according to the present invention.

As shown in FIGS. 1 and 7, the extension tubes 78 may be equipped with wing clamps 82 or another similar flow control apparatus for independently starting, stopping or slowing flow of fluid through the catheter 10. The proximal ends 84 of the extension tubes may be provided with luer connectors suitable for connecting to conduit in communication with a fluid supply device for infusion of fluids or medicaments, for coupling with hemodialysis equipment, for connecting to a fluid-introducing syringe or for similar applications. Exemplary connectors 86 are shown in FIGS. 1 and 7. Preferably, the catheter 10 includes at least two such connectors 86 such that the catheter can be used for hemodialysis.

The catheter of the present invention may be formed according to any suitable method. The preferred method includes the method as shown in FIGS. 6A–6G. As shown in FIG. 6A, a smaller diameter first catheter tube 12 and a larger diameter second catheter tube 26, preferably as described above with respect to the catheter 10, are provided. The small diameter tube 12 is inserted within a second catheter tube 26 such that the tubes are coaxially disposed and spaced from each other, and together the tubes 12, 26 define an annular lumen 40 extending the length of the second catheter tube 26. Preferably, the first tube 12 is inserted in the second tube 26 such that the proximal end 18 and the distal end 20 of the catheter tube 12 extend respectively beyond the proximal end 36 and distal end 38 of the catheter tube 26.

As shown in FIG. 6B, a sleeve 60, as described above, is attached, and preferably molded around the distal portions 16, 34 of the tubes 12, 26 thereby sealing the second lumen 40 at the distal end 38 of the second tube 26 and forming a partially complete structure 88. The sleeve is preferably slid and molded over the distal portions of the tubes such that the distal end of the distal portion 66 of the sleeve is substantially aligned with the distal end 20 of the first tube 12.

Figure 6C:
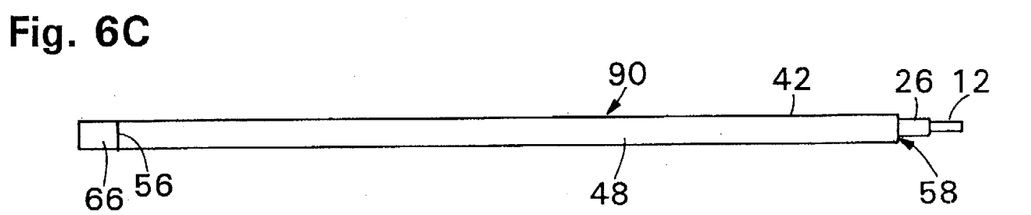

As shown in FIG. 6C, a third catheter tube such as the tube 42 described above is provided. The second catheter tube 26 is placed within the third tube 42 such that the tubes are coaxially disposed and spaced from each other. The third tube 42 and the second tube 26 together define a generally annular third lumen 58 which extends the length of the third tube.

The second catheter tube is preferably inserted in the third catheter tube until the distal portion 66 of the sleeve contacts the distal end 56 of the third tube 42. At this point, the third tube would be substantially covering the proximal portion 64 of the sleeve 60. Preferably, the proximal ends 18, 36 of the first and second tubes extend beyond the proximal end 54 of the third tube. In addition, due to the placement of the sleeve with respect to the third tube, the distal end 56 of the third tube 42 would be positioned between the distal end 16 of the first tube and the distal end 34 of the second tube. The distal portion 66 abuts the distal end 56 of the third tube forming a seam. This arrangement When the sleeve 60 and third tube are molded, the heat blends the seam forming an integral exterior surface 48 as shown in FIGS. 1 and 7.

The third tube 42 is then attached, and preferably molded, to the sleeve 60 to form the structure 90 as shown in FIG. 6C. The proximal portion 64 of the sleeve 60 is attached such that it seals a segment of the third lumen 58 within the distal portion 52 of the third tube which corresponds in length to the proximal portion 64 of the sleeve. The sleeve 60 thereby holds the distal portions of the tubes in a generally coaxial arrangement and seals the second and third lumens 40, 58 in the distal portions 34, 52 of the second and third tubes. The distal end of the third lumen is sealed proximally to the second lumen.

Figure 6D:
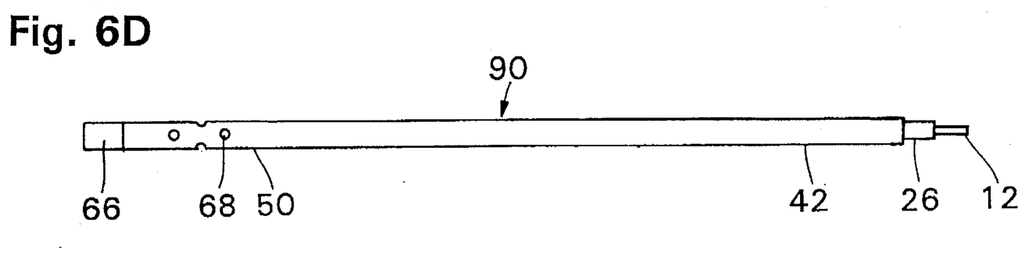

At least one opening 68 is then formed preferably by drilling, through the structure 90 in the distal portion of the third tube 42 proximal to the distal portion 66 of the sleeve. The opening 68 should extend transversely through the third tube 42, the sleeve 60 and the second tube 26 such that the opening is in fluid communication with the second lumen 40 and such that distal end 38 of the second tube is tangent to the opening 68. Preferably, several such openings 68 are spaced from each other around the circumference of the catheter as shown in FIG. 6D.

A second opening 70 is then formed, in the same manner as the first opening 68, in the third tube 42 at a location proximal to the first opening 68. The second opening 70 should extend transversely through the third tube 42 in an area of the third tube proximal to the sealed portion of the third lumen 58 such that the opening is in fluid communication with the third lumen and such that the distal end 56 of the third tube is tangent to the opening 70. Preferably, several such openings 70 are formed around the circumference of the catheter as shown in FIG. 6E.

The distal portion 66 of the sleeve 60 which extends outwardly from the distal end 56 of the third tube to the distal end 20 of the first tube 12 is then formed into a tip 62 as described above for the catheter 10. The tip may be shaped on a mandrel inside of a mold while keeping the distal end of the first lumen 22 open to form a third opening 72 in the tip 62 as shown in FIG. 6F which is coaxial with the first lumen. However, the tip may be formed in accordance with any suitable molding method. The tip 62 may be formed in an alternative shape, such as a blunt end tip or bullet-shaped tip and the opening 72 could be transversely drilled through the distal portion 66 of the sleeve and the distal end of the first catheter tube in fluid communication with the first lumen. More than one such opening 72 may be formed around the circumference of the distal portion (not shown).

Figures 6E, 6F:
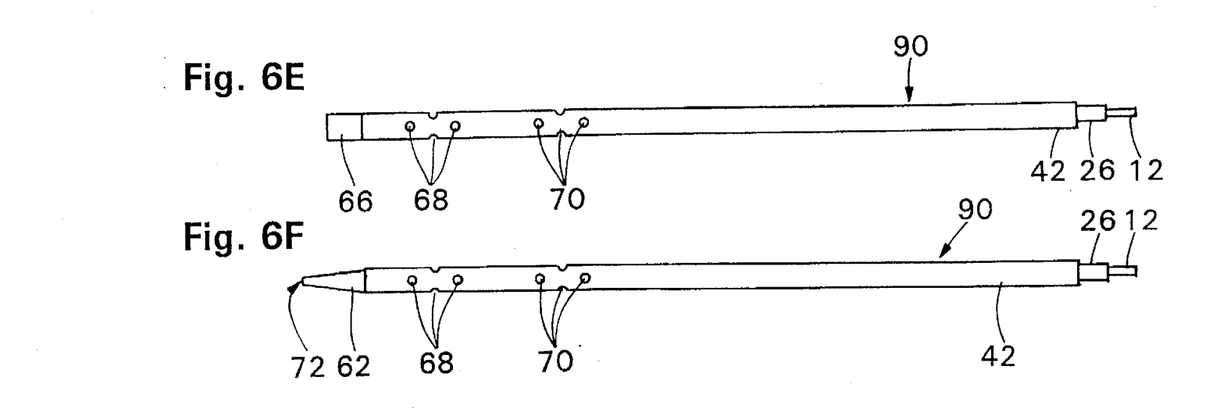

Once the distal portion of the catheter has been assembled as shown in FIG. 6F, extension tubes 78 are provided and a hub 74 is molded around the proximal portions 14, 32, 50 of the catheter tubes 14, 26, 42. Preferably when the hub is molded, passageways 76 are formed in the interior of the hub which are in fluid communication between the lumens 22, 40, 58 and the interior passageways in the extension tubes 78. In order to channel the lumens in separate directions in communication with the tubes, the proximal ends 36, 54 of the second and third tubes are generally diverted as shown in FIG. 5B. This may be accomplished by an insert molding method.

Figure 6G:
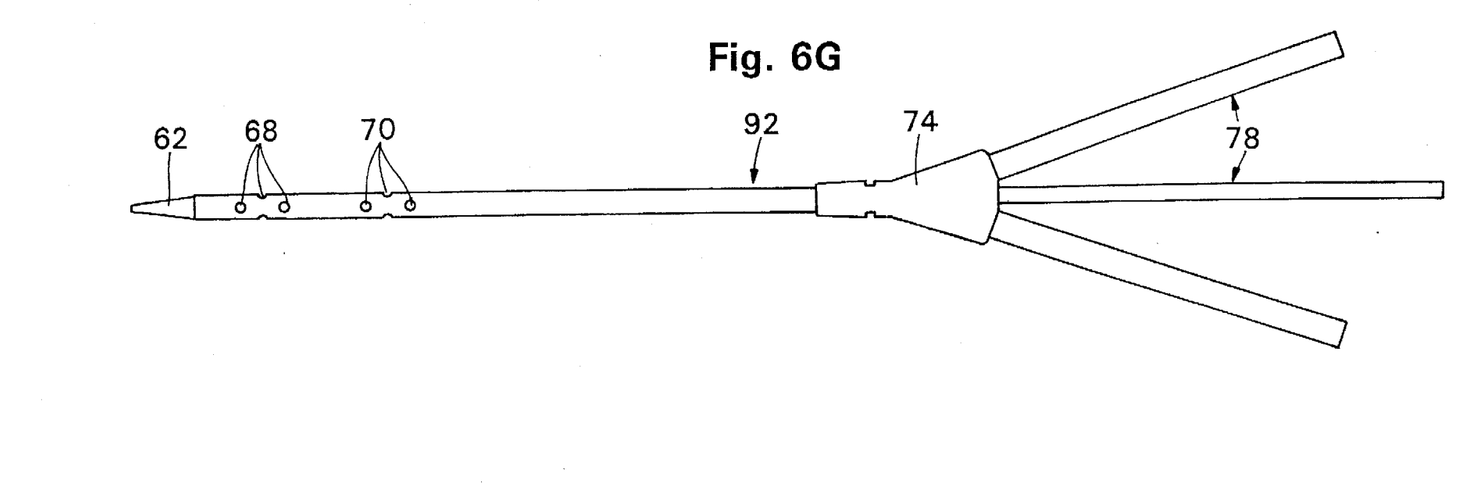

To insert mold the hub, a first straight, pre-shaped metal rod, is inserted within the first lumen 22. An angled, pre-shaped metal rod is inserted in the second lumen 40 such that the proximal end 36 of the second tube 26 is diverted to one side. A second angled, pre-shaped metal rod is inserted in the third lumen 58 such that the proximal end 54 of the third tube 42 is diverted in an opposite direction from the proximal end of the second tube. The ends of the metal rods extend outwardly from the proximal ends of the tubes. The distal ends of the extension tubes 80 are inserted over the extending ends of the metal rods. The structure is then placed in a pre-shaped mold and an injection moldable material is introduced into the mold. Preferably, to ensure a good level of bonding of the hub to the tubing, the hub 74, catheter tubes 12, 26, 42 and extension tubes 78 are all formed of a similar molding material, for example, the Pellethane materials mentioned above with respect to the catheter 10. The mold is cooled and the molded hub removed. The metal rods are then removed from the lumens. Where the rods were placed, the passageways 76 are formed and a structure 92 such as that of FIG. 6G is formed.

While this is the preferred method of making a hub, it should be understood that other methods for molding the hub are within the scope of this invention, including forming separate Y-shaped hubs on the end of each lumen which provide a side passageway for connection of extension tubes. The separate hubs can be bonded together as shown in U.S. Pat. No. 5,053,004 for a dual-lumen coaxial catheter. Based on this disclosure, it would be understood that any suitable molded hub configuration which will hold the proximal portions of the catheter tubes within each other and divert the lumens to flow into the extension tubes would be within the scope of this invention.

Once the structure 92 is formed, suitable connectors 86 may be placed on the end of the extension tubes, and clamps 82 for independently controlling flow in the lumens may be provided to the extension tubes as shown in FIGS. 1 and 7. A suture wing 94 or other similar retaining device can be provided to the hub portion of the catheter 10 as shown in FIGS. 1 and 7 for securing the catheter 10 to a patient when in use. The hub 74 can be molded to have a recess or fitting for receiving such a device. Further, the hub 74 can be molded integrally with such a retaining mechanism (not shown).

It should be understood, based on the above description of the preferred triple lumen configuration as described in detail, that the multi-lumen catheters of the present invention are not limited to three lumens, but could include four or more lumens depending upon the physical constraints of the catheter size and the structural integrity necessary for forming the catheter tubes. When such a multi-lumen structure is formed, the method as described above would merely be repeated by providing additional coaxially disposed catheter tubes around the outermost tube to define a further annular lumen. An additional sleeve would be molded between the two outermost lumens to bond them to the overall catheter structure. Each successive additional sleeve would extend slightly proximal to the prior sleeve in order to facilitate the drilling of access holes in fluid communication with each successive lumen. The hub would be formed with an additionally deflected proximal end being in communication with a further molded passageway and extension tube. The tip would be integrally formed from the sleeves and molded in the manner described above.

Multi-lumen catheters formed in this manner provide the physician with all of the advantages achievable with coaxial flow and significant flexibility with respect to the operation of the device. It is conceivable that by providing such additional lumens, in the event of a single lumen becoming blocked, that the catheter could continue to function by opening flow to an additional lumen and stopping flow to the blocked lumen. Further, medicaments, saline and the like may be introduced during or in the alternative to hemodialysis or other procedures. The multi-lumen catheters are formed to have a flexible, integral tip which has sufficient structural integrity for standard guide wire insertion techniques, and which will, in conjunction with the advantages of the coaxial configuration, minimize trauma to vessel walls and other difficulties associated with side-by-side and similar catheter configurations.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A multi-lumen catheter having a generally coaxial lumen configuration in use, comprising:

(a) a first catheter tube having a proximal portion and a distal portion and defining a first lumen extending longitudinally within the catheter from a proximal end to a distal end of the first catheter tube;

(b) a second catheter tube having a proximal portion and a distal portion and disposed generally coaxially around the first catheter tube, the first and second catheter tubes defining an annular second lumen extending longitudinally within the catheter from a proximal end to a distal end of the second catheter tube;

(c) a third catheter tube having a proximal portion and a distal portion and disposed generally coaxially around the second catheter tube, the second and third catheter tubes defining an annular third lumen extending longitudinally within the catheter from a proximal end to a distal end of the third catheter tube;

(d) a sleeve having a distal portion and a proximal portion, the proximal portion of the sleeve being attached to the distal portions of the first, second and third catheter tubes to hold the first and second catheter tubes within the third catheter tube and to seal the second and third lumens in the distal portions of the second and the third catheter tubes, the third lumen being sealed proximally to the second lumen, the distal portion of the sleeve extending outwardly from the proximal portion of the sleeve to the distal end of the first catheter tube and forming a tip around the distal end of the first catheter tube;

(e) a first opening extending transversely through the third catheter tube, the sleeve and the second catheter tube and in fluid communication with the second lumen;

(f) a second opening extending transversely through the third catheter tube and in fluid communication with the third lumen, the second opening being proximal to the first opening;

(g) a third opening extending through the distal portion of the sleeve and in fluid communication with the first lumen;

(h) a hub having a plurality of passageways, each of the passageways being in fluid communication with one of the first, second and third lumens; and (i) a plurality of extension tubes, each of the extension tubes being in fluid communication with each of the passageways in the hub.

2. The catheter according to claim 1, further comprising a plurality of first openings extending through the third catheter tube, the sleeve and the second catheter tube and in fluid communication with the second lumen, the plurality of first openings being circumferentially disposed around the catheter.

3. The catheter according to claim 2, further comprising a plurality of second openings extending through the third catheter tube and in fluid communication with the third lumen, the plurality of second openings being circumferentially disposed around the catheter and proximal to the plurality of first openings.

4. The catheter according to claim 1, wherein the distal end of the third catheter tube extends outwardly beyond the distal end of the second catheter tube.

5. The catheter according to claim 4, wherein the distal end of the first catheter tube extends outwardly beyond the distal ends of the second and third catheter tubes.

6. The catheter according to claim 1, wherein the third opening extends longitudinally through the distal end of the first catheter tube and is coaxial with the first lumen.

7. The catheter according to claim 1, wherein the catheter further comprises clamps on the extension tubes for independently controlling fluid flow in the extension tubes.

8. The catheter according to claim 1, wherein the catheter further comprises at least two connectors on proximal ends of at least two of the extension tubes.

9. The catheter according to claim 1, wherein the first, second and third catheter tubes comprise a first polyurethane and the sleeve comprises a second polyurethane having a softer durometer than the first polyurethane.

10. The catheter according to claim 1, wherein the tip is frustoconically-shaped.

11. A multi-lumen catheter having a generally coaxial lumen configuration in use, comprising:

(a) at least three generally coaxially disposed catheter tubes having proximal portions and distal portions and defining at least three lumens extending longitudinally within the catheter;

(b) a sleeve having a proximal portion and a distal portion, the proximal portion configured for attaching the distal portions of the catheter tubes together and the distal portion of the sleeve configured for forming a tip around the distal portion of at least one of the catheter tubes;

(c) a hub having at least three passageways, each of the passageways being in fluid communication with each of the lumens;

(d) at least three extension tubes attached to the hub, each of the at least three extension tubes being in fluid communication with each of the at least three passageways; and (e) at least one opening in each of the distal portions of the catheter tubes, wherein each of the openings is in fluid communication with at least one of the lumens.

12. The catheter according to claim 11, wherein there are three catheter tubes, three independent lumens, three extension tubes and three passageways in the hub.

13. A multi-lumen catheter having a generally coaxial lumen configuration in use, comprising:

(a) a first catheter tube having a proximal portion and a distal portion and defining a first lumen extending longitudinally within the catheter from a proximal end to a distal end of the first catheter tube;

(b) a second catheter tube having a proximal portion and a distal portion and disposed generally coaxially around the first catheter tube, the first and second catheter tubes defining an annular second lumen extending longitudinally within the catheter from a proximal end to a distal end of the second catheter tube;

(c) a third catheter tube having a proximal portion and a distal portion and disposed generally coaxially around the second catheter tube, the second and third catheter tubes defining an annular third lumen extending longitudinally within the catheter from a proximal end to a distal end of the third catheter tube, wherein the distal end of the third catheter tube extends outwardly beyond the distal end of the second catheter tube and the distal end of the first catheter tube extends outwardly beyond the distal ends of the second and third catheter tubes;

(d) a sleeve having a distal portion and a proximal portion, the proximal portion of the sleeve being attached to the distal portions of the first, second and third catheter tubes to hold the first and second catheter tubes within the third catheter tube and to seal the second and third lumens in the distal portions of the second and third catheter tubes, the third lumen being sealed proximally to the second lumen, the distal portion of the sleeve extending outwardly from the proximal portion of the sleeve to the distal end of the first catheter tube and forming a frustoconically shaped tip around the distal portion of the first catheter tube;

(e) a plurality of first openings circumferentially disposed around the catheter and extending transversely through the third catheter tube, the sleeve and the second catheter tube, the plurality of first openings being in fluid communication with the second lumen;

(f) a plurality of second openings circumferentially disposed around the catheter and extending transversely through the third catheter tube, the plurality of second openings being in fluid communication with the third lumen and proximal to the plurality of first openings;

(g) a third opening extending longitudinally through the distal end of the first catheter, the third opening being coaxial with and in fluid communication with the first lumen;

(h) a hub having a plurality of passageways in independent fluid communication with the first, second and third lumens; and (i) a plurality of extension tubes, each of the extension tubes being in fluid communication with each of the passageways in the hub.

* * * * *